United States Patent [19]
Kidwell et al.

[11] Patent Number: 5,891,649
[45] Date of Patent: Apr. 6, 1999

[54] REAL-TIME BIOCHEMICAL ASSAY TELEMETERING SYSTEM

[75] Inventors: David A. Kidwell, Alexandria, Va.; Gil F. Richards, Duarte, Calif.; Roger G. Kern, Pasadena, Calif.; Frederick W. Mintz, La Canada, Calif.

[73] Assignee: California Institute of Technology, Pasadena, Calif.

[21] Appl. No.: 769,664

[22] Filed: Dec. 19, 1996

Related U.S. Application Data

[63] Continuation of Ser. No. 694,923, Aug. 8, 1996, abandoned.

[51] Int. Cl.$^6$ .................................................. G01N 33/533
[52] U.S. Cl. ................................ 435/7.9; 422/55; 422/56; 422/58; 422/60; 422/82.05; 422/82.09; 422/99; 435/7.1; 435/7.8; 435/7.92; 435/7.93; 435/7.95; 435/287.2; 435/287.7; 435/287.8; 435/961; 436/518; 436/538; 436/541; 436/805
[58] Field of Search .................................. 422/55, 56, 58, 422/60, 82.05, 82.09, 99; 435/7.1, 961, 7.8, 7.9, 7.92, 7.93, 7.95, 287.2, 287.7, 287.8, 287.9, 288.7; 436/518, 538, 541, 805

[56] References Cited

U.S. PATENT DOCUMENTS

| | | | |
|---|---|---|---|
| 5,340,748 | 8/1994 | Baugher et al. | 436/518 |
| 5,369,007 | 11/1994 | Kidwell | 435/7.9 |
| 5,520,787 | 5/1996 | Hanagan et al. | 204/409 |

*Primary Examiner*—Christopher L. Chin
*Assistant Examiner*—Bao-Thuy L. Nguyen
*Attorney, Agent, or Firm*—Fish & Richardson P.C.

[57] ABSTRACT

The present invention is an apparatus and a method of detecting a chemical released by perspiration, typically through sweat and broadcasting the detection to a receiver. The chemical may be a drug of abuse. The device which is attached to the skin of a subject contains labeled antibodies or label containing microspheres attached to antibodies. The labeled antibodies are bound to solid phase drug via antigen-antibody interaction. These labeled antibodies are displaced from the solid phase support to which they are bound by free drug molecules in the perspiration. These labeled antibodies then migrate through a spacer layer and are trapped by a layer containing a suitable selective binding material. The label is illuminated or excited by a light source and detected by a photodetector. The signal can be recorded, or transmitted to a remote radio monitor.

20 Claims, 6 Drawing Sheets

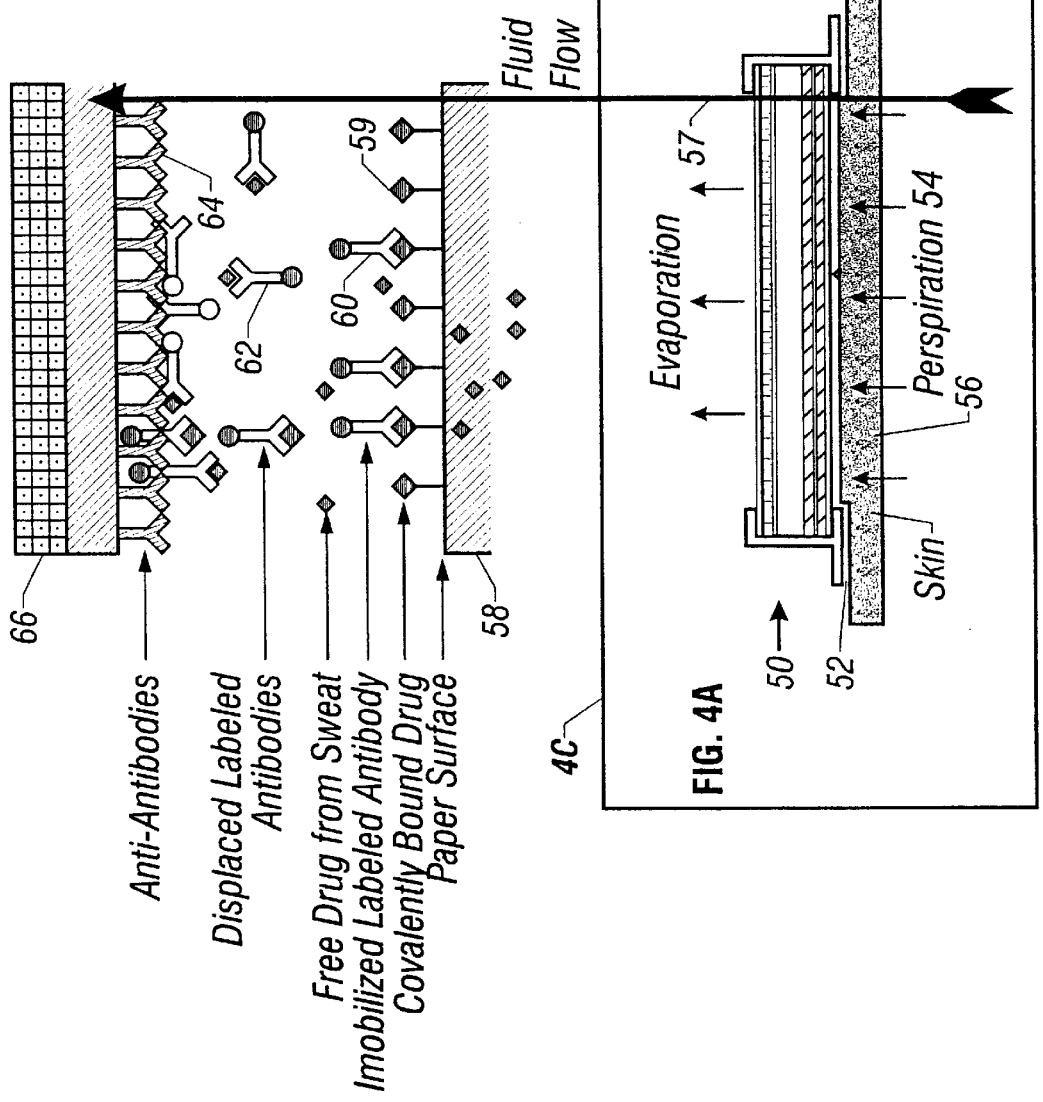
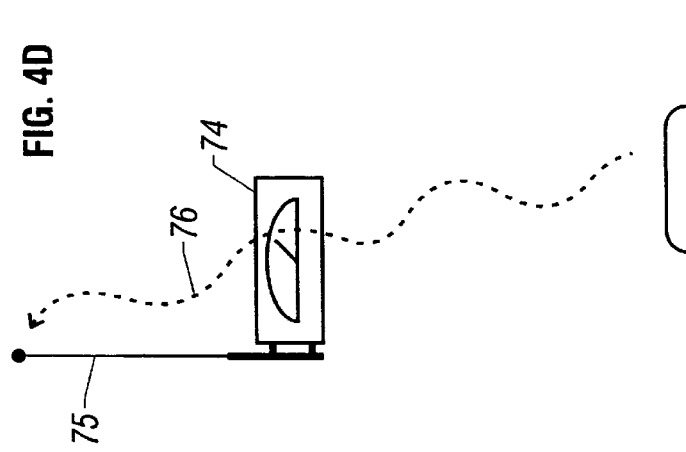

*Perkin-Elmer 650-15 Fluorescence Spectrophotometer

REAL-TIME BIOCHEMICAL ASSAY TELEMETERING SYSTEM

The application is a continuation to refer to the filing date of prior application Ser. No. 08/694,923, filed Aug. 8, 1996, now abandoned. The prior application was abandoned on Dec. 24, 1996, after the filing of the present application on Dec. 19, 1996.

ORIGIN OF THE INVENTION

The invention described herein was made in the performance of work under a NASA contract, and is subject to the provisions of Public Law 96-517 (35 USC 202) in which the Contractor has elected to retain title.

BACKGROUND OF THE INVENTION

1. Field of the Invention

The present invention relates to a process and apparatus for the detection of drugs and other biochemicals present in a human or other mammalian system and the reporting of the detection telemetrically to a receiver. The present invention is particularly suited for monitoring parolees and others for drug use, monitoring medical conditions of patients, and remote monitoring of biochemical parameters of subjects in space.

2. Background Art

Agencies of the criminal justice system utilize a variety of techniques for monitoring convicted persons either in institutions or in various less secure settings within the community. One successful method for monitoring convicts in a non-institutionalized setting employs a telemetry bracelet for locating persons at home or at work locations. In these systems, a device attached to the paroled convict signals a receiver attached to a telephone system to report the convict's whereabouts relative to the receiver. Parole conditions may also include prohibitions on the use of controlled substances, especially in cases of convictions involving drug use. Additionally, convicts who are incarcerated are also supposed to be prohibited from using controlled substances during incarceration. Due to manpower and budgetary constraints, only a small fraction of the existing parolees can be tested for drug use at any one time. Therefore, for these types of situations, it would be desirable for telemetry devices, similar to those presently being used for the parolees, such as telemetry bracelets, to actively monitor for the presence of controlled bioactive substances in a non-invasive and continuous way.

In a medical setting, hospitals and home care medical care operations require that various biochemical parameters be carefully monitored. For example, diabetics must control their blood sugar levels and blood insulin levels carefully. Patients with infections must maintain a minimum antibiotic level in their system. Patients with various chronic ailments are required to take regular doses of medication, such as epileptic patients on anti-epileptic drugs. The continuous and non-invasive monitoring of such patients is also desirable. The medical community may also find it desirable to monitor the levels of prescribed medications and detect overdoses of such medications in order to come to the aid of such patients as soon as the problem is detected.

Such sensor/telemetry technology has applications to NASA activities as well where biological substance detection could be employed in process control for life support systems and in the remote manipulation and analysis of space borne biological and medical experiments.

Liotta, U.S. Pat. No. 4,837,145 discloses a device for determining the presence of an antigen which comprises a trapping zone, which contains material capable of capturing free flowing enzyme linked antibodies, but not antibodies bound to a transport particle which flows freely through the trapping zone into the substrate zone, and a substrate zone which contains material capable of reacting with enzyme-linked antibodies to produce a reaction which indicates the presence of antibodies. A method of determining the presence of an antigen is also disclosed wherein a sample is mixed with two classes of antibodies which are specific for the antigen being tested for, but which react with different antigen domains, wherein the mixture consists of class one antibodies bound to a transport particle which flows freely through the trapping zone and class two enzyme-linked antibodies which are incapable, unless bound to the transport particles, of flowing freely through the trapping zone. In the presence of the antigen being tested for, both classes of antibodies bind to the antigen and flow through the trapping zone into the substrate zone, wherein a reaction takes place to indicate the presence of the antigen.

Liotta, U.S. Pat. No. 4,446,232 discloses a device for determining the presence of antigens which comprises a first zone containing antigens and enzyme-linked antibodies which are capable of immunologically reacting with said antigens, said antibodies being positioned in said first zone such that they will be removed from said first zone when reacted with antigens passing through said first zone but not removed from said first zone in the absence of such antigens, and a second zone containing material capable of reacting with said enzyme-linked antibodies to produce a color forming reaction which indicates the presence of said antibodies. Hiratsuka et al., U.S. Pat. No. 4,337,065 also discloses a multilayer device for determining antigens similar to U.S. Pat. No. 4,446,232 except for the detection being by development of a silver halide film.

In 1991, Dr. David Kidwell reported the development of a simple to use device for field testing urine and saliva for the presence of drugs of abuse, specifically, cocaine. The device is called a microassay on a card, or MAC. It consists of a small flat plastic card (2 inches×2 inches×0.2 inches) in which all of the reagents required for the cocaine assay are provided. To run the test, a sample of saliva or urine, 50 $\mu$l, is placed in a well; the urine or saliva is drawn through a semipermeable membrane into the MAC via capillary action. If the drug is present, a calorimetric reaction occurs and becomes visible within 5 minutes on the card. The MAC test is more fully described in U.S. Pat. Nos. 5,200,321 and 5,369,007, incorporated herein by reference. As described in U.S. Pat. No. 5,200,321, the microassay card includes an upper layer containing wells for receiving a liquid sample, a second layer of the card, beneath the first layer, which includes a supporting surface bound to a reactive species, and a third layer which includes an absorbent support impregnated with an indicator. Typically, the indicator is a substrate for an enzyme, such as a reduced dye precursor and a source of hydrogen peroxide necessary for the action of the enzyme upon the substrate to cause a spectral change in the absorbent layer. The microassay card is particularly useful for drug testing.

The MAC operates by virtue of an antibody-antigen interaction. Disposed within the MAC is an absorbent paper layer to which a drug sample (antigen) is covalently bound. Enzyme labeled anti-drug antibodies are immobilized on this layer by an antigen-antibody interaction. If the drug to be detected is present in the saliva or will displace the bound anti-drug antibody, which then can travel through the system and reach a layer of substrate. The enzyme attached to the antibody causes the substrate to change color, giving a visual signal for presence of the drug.

It would thus be desirable to provide a system which integrates the microassay system with a sensor/telemetry system with a wide range of potential applications. The applications are limited then only by the availability and stability of the biological reporter molecules such as antibodies, enzymes, and the like.

SUMMARY OF THE INVENTION

The present invention comprises, in its preferred embodiment, a method and apparatus for detecting drugs or other biochemicals or chemicals from the perspiration (perspiration being defined as both sweat and sebaceous secretions) of individuals and reporting the results of the detection remotely. The apparatus of the present invention comprises a series of polymer layers containing antibodies which specifically bind substances of interest and which are induced to migrate from sites of immobilization to sites of detection by molecules which have displaced the labeled antibody from its immobilization site by competitively binding to it. These polymer layers can be packaged in laminate form or can exist in separate packages which are then fluid flow connected by tubing or other conduit. A reporter molecule coupled reaction linked to the migrating antibodies then alters the light emission of the most distal polymer layer which interfaces to the photodiode-based illumination/detection electronics and logic. The substance detection algorithm initiates a reporting sequence to the telemetry subsystem if the drug or other substance were present.

It is an object of the present invention to provide a chemical detection and signaling system which detects the transpiration of substance(s) of abuse using a driven biochemical detector specific for the substance.

It is a related object of the present invention to provide such a system having performance characteristics applicable to the continuous (real-time) monitoring of drugs in sweat.

It is another object of the present invention to utilize an electronic interface capable of translating that signal into electronic form suitable for transmission to a remote monitoring station.

Drug Badge Design
Biochemical System

The present invention utilizes the following information based upon the fact that most drugs are eliminated from the body in significant amounts by the sweat glands (see Table 1).

TABLE 1

MEASURED DRUG CONCENTRATIONS IN PERSPIRATION*

| DRUG | CONCENTRATION ($\mu$g/ml) | RANGE ($\mu$g/ml) |
|---|---|---|
| Methamphetamine | 1.4 | 0.88–1.42 |
| Morphine | 1.5 | 0.31–2.7 |
| THC | 0.32 | 0.034–1.0 |
| Benzodiazepine | 0.19 | 0.14–0.33 |
| Cocaine | 9 | 1–50 $\mu$g/$\mu$l** |
| Barbiturate | 70 | 66–74 |
| Methadone | 0.48 | 0.31–0.86 |
| Cotinine (nicotine metabolite) | 0.51 | 0.10–0.93 |

*S. Balabanova, and E. Schneider: "Nachweis non Drogen im Schweiss", Beitrage Zur Gerichtlichen Medizin, 48 (1990) p. 45–49.

TABLE 1-continued

MEASURED DRUG CONCENTRATIONS IN PERSPIRATION*

| DRUG | CONCENTRATION ($\mu$g/ml) | RANGE ($\mu$g/ml) |
|---|---|---|

I. Ishiyama, et al: "The Significance of Drug Analysis of Sweat in Respect to Rapid Screening for Drug Abuse", Z. Techtsmed. 82 (1979) p 251–256.
**G. I. Henderson, M. R. Harkey and R. Jones, "Final Report-Hair Analysis for Drugs of Abuse", National Institute of Justice, Grant #90-NIJ-CX-0012, Sept, 1993.

The drug badge of the present invention consists of a wristwatch or adhesive bandage ("Band Aid®")—like device that is attached to the skin. Sweat from the skin passes into the drug detection patch through a semipermeable membrane. Only small molecules (drug, water, salts, etc.) will pass through the membrane; large molecules and bacteria will be excluded. While the device will work without this membrane, its presence assures sterility and provides flow rate control through the device.

The apparatus of the present invention contains small fluorescent or enzyme labeled antibodies which are bound to solid phase drug. These labeled antibodies will be displaced from the solid phase support to which they are bound by any free drug molecules in the sweat. These labeled antibodies can then migrate through a moist layer (such as filter paper) to the distal side of the badge (driven by transpiration) and be trapped by a polymer layer containing anti-antibodies, or other suitable trapping material. The three layers of: solid phase label, spacer, and trap, form a Biochemical Diode-Capacitor (BDC) which is discussed in detail below. The BDC prevents the label from backflowing, concentrates the signal into a small volume, and allows the signal to be integrated over time. The fluorescent or calorimetric signal is excited by a light source and detected by a photodetector. Alternatively, the change in reflectance due to the presence of the calorimetric material is sensed by a photodetector. The signal can be recorded or transmitted to a remote radio monitor.

The device may also incorporate electronics for the measurement of skin temperature, skin conductivity and/or pulse rate. Although these variables change with exercise and day-to-day activities, the rate of change and the duration of change can indicate the presence of stimulants or depressants in the body. Such a combination sensor monitoring may reduce the false positive rate of each individual sensor. Alternatively, only a single sensor may be employed under certain applications. For example, if it is desirable to monitor an individual remotely and only determine stimulant use (by drugs such as cocaine or amphetamines), pulse rate monitoring may be satisfactory. If the pulse rate did not increase for a given period, then that individual need not be summoned for more extensive testing. If the pulse rate increased, then further testing could be used to determine if the pulse rate increase was due to drugs or other causes. Simple sensors can reduce the need for testing with the cost trade-off being the cost of the sensor array versus the cost of summoning the individual and performing more extensive testing. These sensors can also aid in determining removal of the device because the body temperature will drop or the pulse rate will be lost.

Electronic Interface

The system for monitoring the color change signal consists of a light source illuminating the appropriate polymer layers and a series of photodetectors with associated electronics to detect changes. The detector and light modulation circuitry provides pulse modulation to reduce effects of ambient light false triggers. Other detection precautions employed in the signal detection system will consist of comparing several cells for a change prior to triggering an alarm. For a confidence and calibration test, some cells that do not change are monitored and compared continuously. After a change is detected, a modulation signal turns on a small transmitter. The signal from this transmitter is detected at a remote monitoring site. To accommodate the monitoring of several people, the signal can be provided with a special code for each user. The device may also be supplied with a means for signaling the removal of the device so that, for example, a drug user cannot remove the device to avoid detection of chemicals in the sweat. Long distance transmission is very power intensive. The detector and transmitter and remote receiver may have an intermediate device to save power. The wrist size device may have a low power transmitter which transmits to a receiver close by or on the individual. This intermediate transmitter may contain a storage device to save sensor readings and record the positional location of the individual before interrogation by the remote site.

BRIEF DESCRIPTION OF THE DRAWINGS

FIGS. 4a–d illustrate an overall schematic view of the operation of the badge of the present invention for the target drug including the detection and telemetry systems.

DETAILED DESCRIPTION OF THE INVENTION

Figure 1:
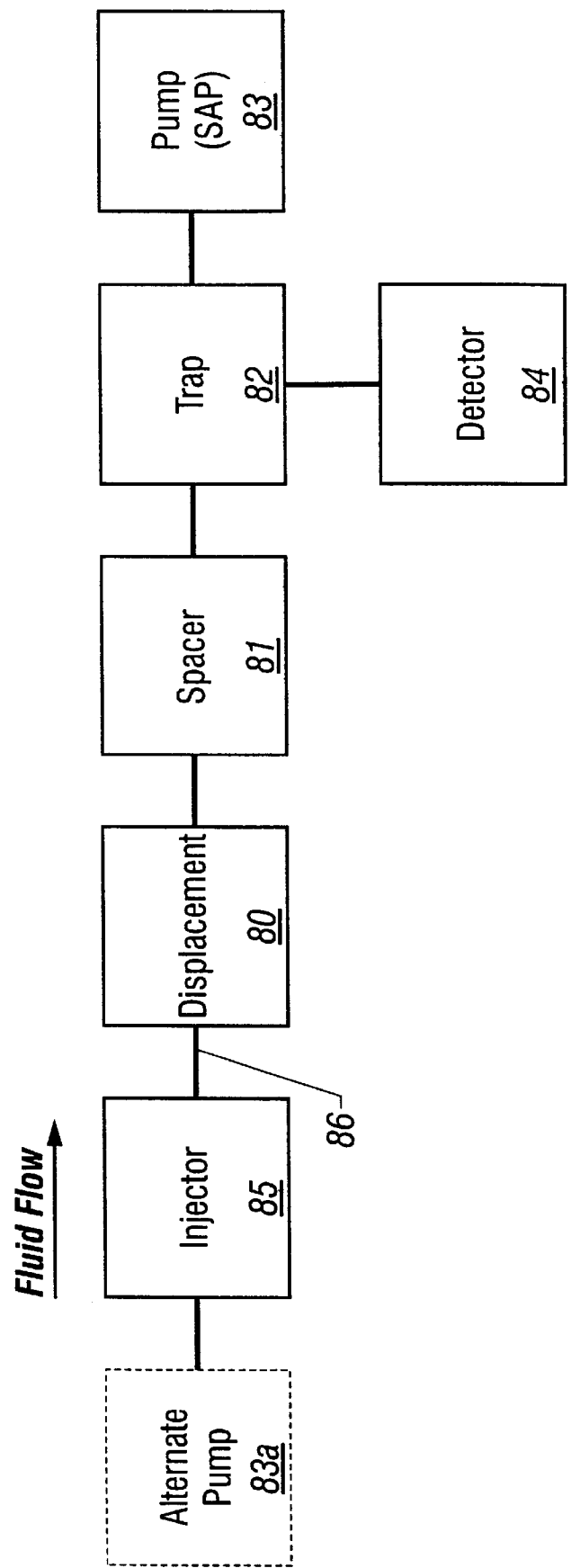
FIG. 1 is a schematic block diagram of the relationship of the basic components of the present invention.

The present invention includes a "BDC" or "Biochemical Diode-Capacitor", the seven components of which are depicted in FIG. 1. The name "BDC" is derived by analogy to an electronic circuit containing a diode connected to a capacitor which permits one-way current flow and thus the storage of charge in the capacitor. Another term for such an electronic circuit (and by analogy the BDC) is "integrator". The BDC is a fluid flow control device which allows signal molecules to flow from the sample part of the device to be trapped/concentrated at the detector part of the device: allowing the signal to be integrated over time.

The following is an explanation of the seven components of the schematic/block diagram which is FIG. 1. The three central components are the Displacement 80, the Spacer 81, and the Trap 82 components. These components can be connected directly together to allow fluid flow, or can be connected by a fluid channel of some sort such as tubing. These connections are generalized by the line labeled 86 in FIG. 1. The displacement component 80 contains labeled anti-drug antibodies which are held in place by solid phase bound drug (antigen). The label can be fluorescent, phosphorescent, enzyme, dyed-microsphere or other antibody label commonly used by those well versed in the art.

The functional roles of antibody-antigen can also be reversed if desired; that is, the drug molecule can be labeled and held in place by antibody bound to the solid phase; it would be the labeled drug that would then be released by free drug (in a sample) and would migrate to the trap layer to be detected. The trap in that case would consist of a component to bind to the label or to the label carrier, the carrier being either the drug itself or another component such as microspheres. The microspheres can contain other groups besides the label such as proteins, ion exchange groups and sugars that can bind to the trap component. In the descriptions to follow, the focus will be on the drug as bound to the solid phase and the antibody containing the label: it is always implied that the reverse case is just as acceptable even if not explicitly stated. It will also be understood that while the present invention is described in terms of drug detection, any chemical which is bindable to an antibody or other bioconjugate may be detected in accordance with the present invention.

Component 81 is a Spacer separating the Displacement 80 and the Trap 82 components. The Spacer 81 optically and biochemically isolates these two components (80 & 82). The Spacer can be made of polymer material such as common filter paper for use in a laminate form of the BDC or can be tubing made of polyethylene or other common plastic, or metal for use in a pumped flow-through form of the BDC. The optical/biochemical isolation function of the spacer 81 can be incorporated into the displacement layer through proper choice of displacement layer materials and chemical procedures. For example, a sufficiently thick filter paper derivatized on one side with covalently bound drug and antigenically bound labeled antibody could effectively act as the spacer layer 81 when oriented with its underivatized side toward the trap layer 82: optically/biochemically isolating the antigenically bound labeled antibody from the trap 82 and detector layers 84. Component 82 is the label Trap. The trap restrains movement of labeled antibody through the BDC enabling increased fluorescent signal to be presented to the detector. The trap is made up of derivatized polymer such as filter paper or polymer beads containing chemical or biological active groups that can bind the labeled antibody. Examples of such groups are: anti-antibodies, protein-A, protein-G, lectin (such as Concanavalin-A), and ion exchange groups. Additionally, while the binding molecule for binding the drug in the presently preferred embodiment is an antibody, it will be recognized that other binding molecules can be utilized without departing from the spirit and scope of the present invention. The method of chemically coupling these biologically active groups to polymers is commonly known to those well versed in the art. The Trap 81 can also physically restrain the labeled antibodies by molecular sieving action as with dialysis tubing or other small pore filter material. The trap 82 can also perform the functions of the spacer layer 81 with proper choice of materials and chemical procedures. For example, a trap layer consisting of sufficiently thick, dark filter paper derivatized on one side with anti-antibodies could effectively act as a spacer layer when oriented with its underivatized side toward the displacement layer 80. The Detector 84 detects the optical signal trapped in 82. The detector consists of a light source and optical detector pair with associated optical filters. The filters can be narrow band interference filters or can be monochromators made up of diffraction gratings or prisms or be plastic colored filters such as sold by Kodak under the Wratten trademark.

Examples of light sources are: LEDs (light emitting diode), laser diodes, and light sources commonly used in spectrofluorimeters and spectrophotometers (xenon lamps, carbon arcs, tungsten bulbs). Examples of detectors are: photodiodes, phototransistors, and photomultiplier tubes.

The Pump 83 or Alternate Pump 83a component forces fluid through the BDC system. This allows label released from the Displacement 80 component to travel through the Spacer 81 to the Trap 82 where it is viewed and detected by the Detector 84.

Figure 5:
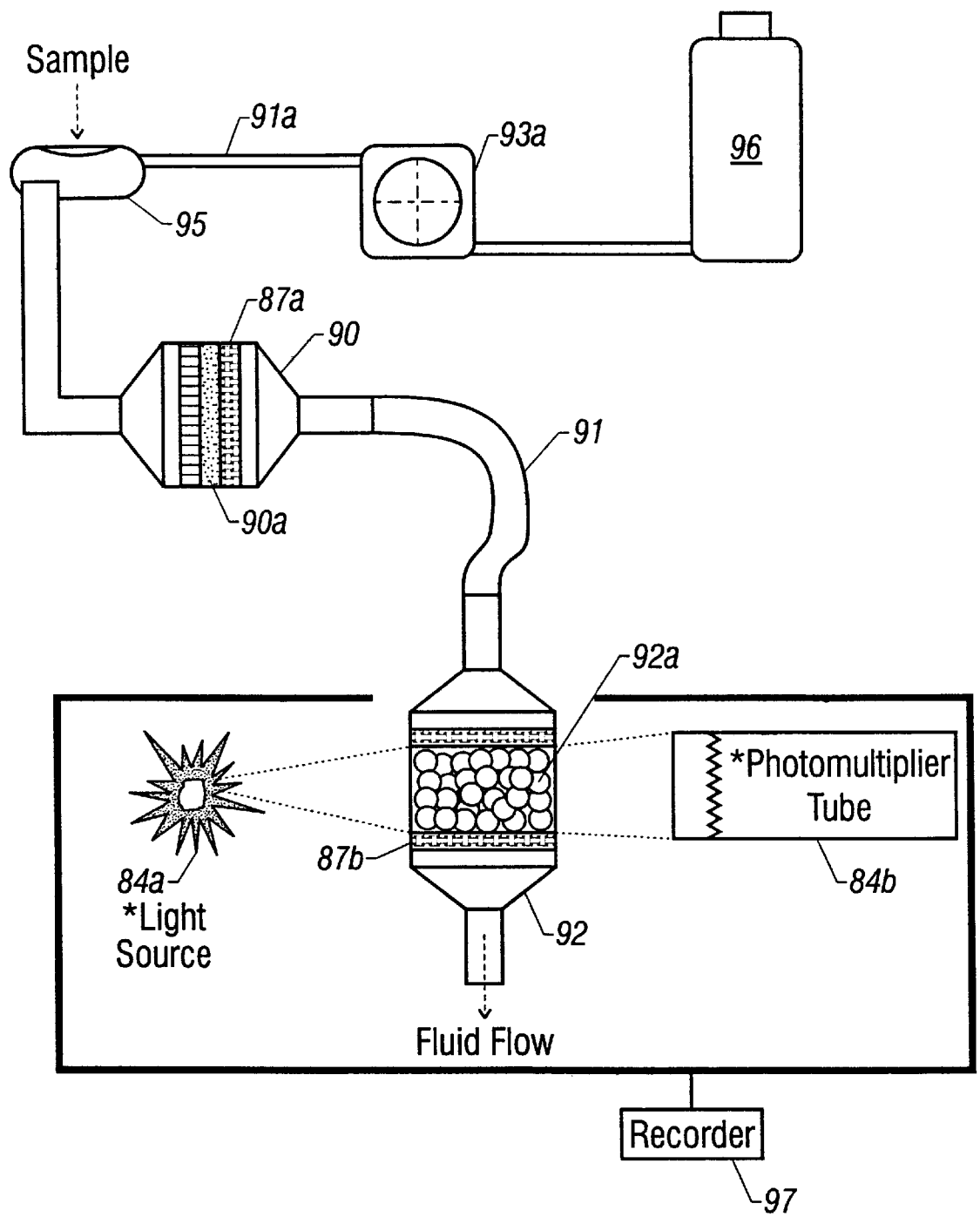
FIG. 5 is a schematic of an operational example of the present invention in Pumped Flow-Though mode.

FIG. 1 gives the overall relationship of the different components that make up the BDC. In actual implementation, the BDC can be described as existing in three manifestations or "modes". These modes depend upon the pumping system chosen. The first one is the "Pumped Flow-Through" mode and consists of an active pump—the Alternate Pump 83a component in FIG. 1—and an active injector—the Injector 85 component—for applying sample to the system. An example of this mode is shown in FIG. 5 and will be described in more detail later. The second mode is the "Saturation" mode where the Pump 83 component consists of SAP (superabsorbent polymer). The SAP will draw fluid through the system until its maximum fluid capacity is reached. This mode is shown in FIG. 3 and its accompanying text. The third mode is the "Transpiration" mode which also uses SAP for a Pump 83 component, but in this case evaporation from the SAP surface allows continual flow through of fluid. The SAP is an optional component that may be replaced by more conventional absorbents such as filter paper. This is discussed in more detail in the text associated with FIG. 2.

In both the second and third modes, the Injector 85 can be considered to be the BDC to a sampled surface interface.

Figure 2A:
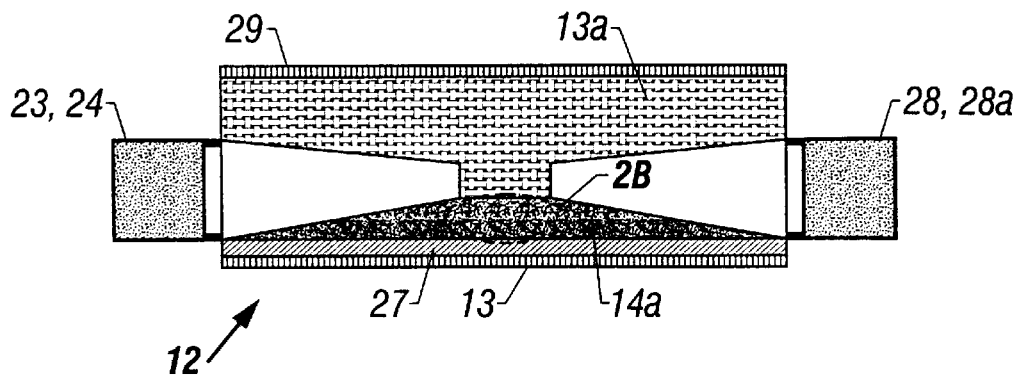
FIGS. 2a–b is a schematic functional diagram of the arrangement and operation of the transpiration driven laminate form of the present invention.
Figure 2B:
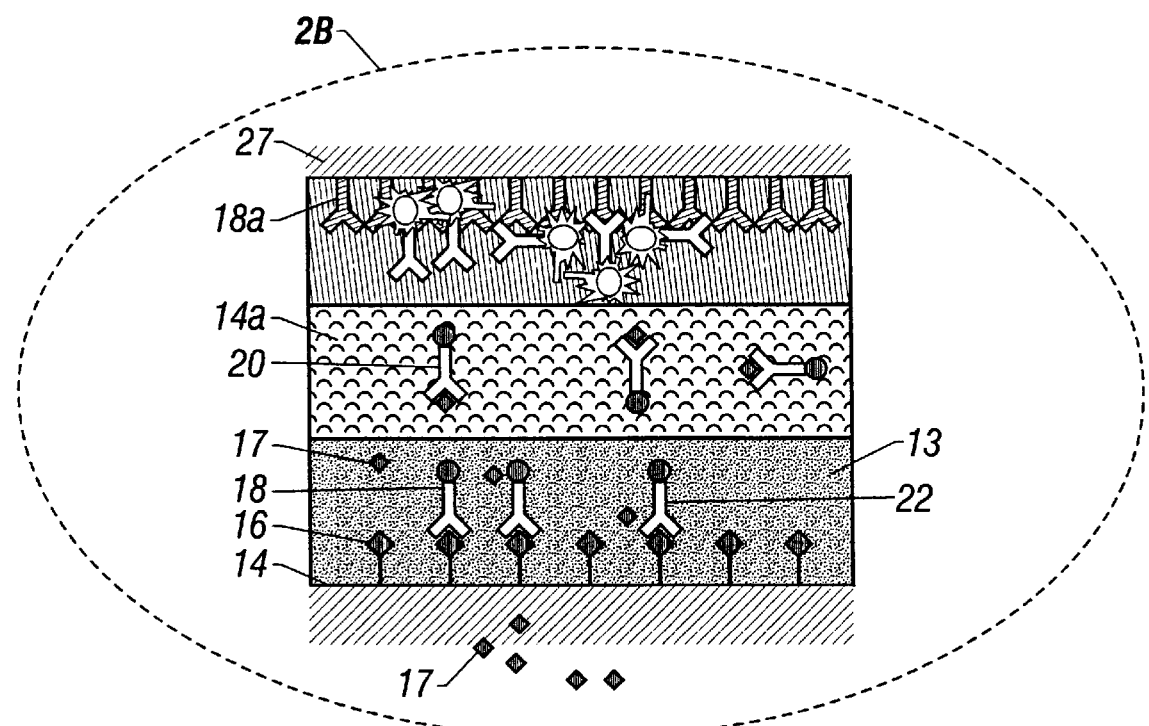
Figure 3:
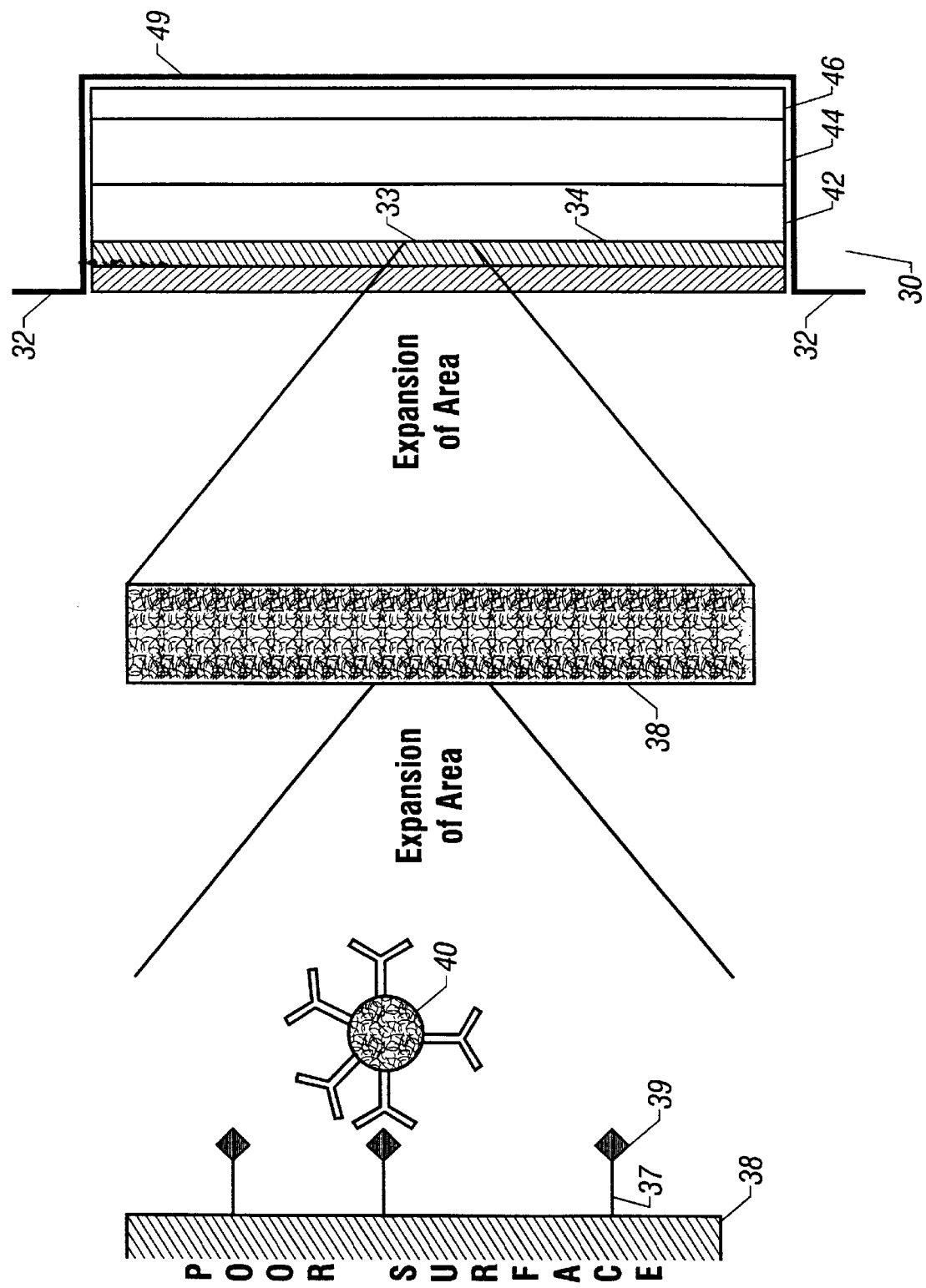
FIG. 3 is a schematic view of the operation and structure of a "saturation mode" form of the badge of the present invention and the detection system for the target drug.

FIG. 2 depicts in schematic form the present invention as a perspiration monitoring badge using the "Transpiration Mode" BDC. Starting from the proximal surface of the present invention, the first element is a semipermeable membrane 12 which excludes high molecular weight components of sweat (including particles and aggregates), maintains sterility, and allows flow of small molecules and water into the device. Semipermeable membranes are known in the art, and presently, the preferred embodiment is made of polycarbonate and can be obtained from commercial sources such as Nucleopore (Pleasanton, Calif.) or Poretics Co. (Livermore, Calif.)

Bound to a solid polymer support 14 is a layer or area of covalently bound drug 16 which holds labeled antibodies in place. This area is made from various drugs or drug analogs which are bound to a chemically derivatized paper or other polymer. An example of such covalently bound drug is amphetamine bound to carbonyldiimidazole activated paper. Commercial sources of drugs and drug analogs, activation chemicals, and activatable papers for the covalent bonding, are available from various companies, including Sigma Chemical Co. and Pierce. 14, 16 & 18 comprise the Displacement component of the BDC. (See also U.S. Pat. No. 5,196,302, incorporated herein by reference). Free drug 17 from sweat is also depicted. The next layer is the spacer 14a which optically and biochemically separates the displacement component from the trap component and can be composed of similar base material as support 14.

In the next layer 27 are bound anti-antibodies 18a which capture and hold displaced labeled antibodies 20 which have formerly free drug bound to it. These anti-antibodies may be, for example, rabbit or goat anti-mouse IgG, as is well known in the art. Commercial chemical supply companies such as Sigma Chemical Co. and VWR are sources of the anti-antibodies. Layer 27 can be made of polymer similar to layer 14. Elements 27 & 18a constitute the Trap component of the BDC.

The labeled antibodies 22 are drug specific antibodies that carry a fluorescent dye marker or other marker, such as enzymes capable of providing optically readable signals when provided with a substrate, colloidal particles, polystyrene latexes and other markers known in the art. In the presently preferred embodiment, the labeled antibodies are drug specific mouse monoclonal antibodies (of Fab fragments of these antibodies), conjugated with Texas Red fluorescent dye. Mouse monoclonal anti-drug antibodies, or polyclonal anti-drug antibodies are available from a number of sources including Sigma. Texas Red dye conjugation systems are available from Molecular Probes, Inc.

The next element of the present invention is an optical filter 23 which functions to reduce background and increase sensitivity by allowing only a narrow wavelength band of light (centered near 615 nanometers) to reach the photodetector. An example of such a filter is an interference filter made by vacuum deposition of dielectric layers-of glass as is commercially available from Edmund Scientific Co.

A photo-detector 24 is supplied to detect an optical signal and transduce it into an electrical signal for further processing. For use with a Texas Red dye, the photodetector detects a light emission wavelength of 615 nanometers. It will be obvious to persons or ordinary skill in the art that the photodetector can be selected for sensitivity to the appropriate emission of the fluorescent or calorimetric signal to be provided by the system selected for the present invention, many of which are known in the art. In the preferred embodiment of the present invention, for use with the Texas Red dye, a Mercury-Cadmium Telluride photodiode obtainable from New England Photoconductor may be used.

The next element of the present invention is an LED (Light Emitting Diode) 28 which functions to excite the Texas Red Dye. Included with the LED is a filter 28a similar to filter 23 except that it has a passband centered on the Texas Red excitation wavelength of 595 nanometers. The LED of the present invention is a yellow light emitting silicon diode which can be obtained from various electronics companies including Motorola, Texas Instruments and the like. It will be obvious to persons of skill in the art that other LEDs or excitation means can be utilized without departing from the spirit of the present invention, and further, that the particular LED selected can be chosen to coincide with the dye or other signal means used without undue experimentation.

The next element of the present invention is the superabsorbent polymer (SAP) 13a layer. In the presently preferred embodiment, the polymer is made from derivatives of polyacrylic acid. This composition can be obtained from a number of commercial sources. The SAP 13a layer and the semipermeable membrane 29 form the transpiration pump that drives fluid through the system. Evaporation through the semipermeable membrane prevents irreversible SAP saturation.

FIG. 3 is an illustration of the application of the present invention as a perspiration monitoring badge for drugs of abuse using the "Saturation Mode" BDC, and is shown in schematic format. More particularly, FIG. 3 shows the invented badge, an enlargement of a portion of the badge and an enlargement of a portion of the enlargement, as explained in more detail below. The badge 30 has a generally rectangular cross-section. On the surface of the badge 30 is an adhesive layer 32 which attaches the badge to the skin. While an adhesive attachment is not essential, and other attachment means such as a mechanical attachment can be used, and adhesive attachment provides a secure attachment system. The first layer is a semipermeable membrane 33 which acts as a protectant and a vapor barrier to permit only small molecular weight molecules into the badge system, including the sweat and any drug to be detected, and to entrap the transpired sweat into the badge once it permeates the membrane. Layer 33 is optional. The next layer of the badge is an absorbent paper 34 containing immobilized drug and bound spheres, described in more detail below. Element 38 is an enlarged view of a portion of the absorbent paper 34 showing that the paper has distributed throughout it covalently bound drug and immobilized antibody labeled microspheres.

As mentioned above, FIG. 3 also has an enlargement of a portion of the absorbent paper with the covalently bound drug and fluorescent microsphere labeled antibody. In the presently preferred embodiment, the labeled antibodies are drug specific mouse monoclonal antibodies conjugated to polystyrene latexes which are fluorescently labeled. The polystyrene latexes termed TransFluoSpheres available from Molecular Probes, Inc. are preferred with the 633/720 version most preferred. Specifically, the paper 38 has the drug 39 covalently bound to it through linkage 37. The fluorescent labeled antibody 40 is bound through standard antibody-antigen binding to the drug. As explained previously, when drug molecules are present they compete with the immobilized drug for binding sites on the labeled antibody, causing the antibody to be released from the immobilized drug, and migrate through the badge system as described in more detail below.

Returning to the schematic of the badge, the next layer is a layer of blotter paper and screen 42 which forms the Spacer component (see 81 of FIG. 1) of the BDC. The next layer is the superabsorbent polymer 44 which has been previously described. The SAP may be replaced by filter paper which may also act as an absorbent when sweating is light. In this case the SAP has the additional function of acting as the Trap component (82 FIG. 1) of the BDC, since the microspheres become immobilized in the sieve-like polymer matrix. The next layer is a tissue layer 46, and finally a transparent plastic layer 49 which acts as a protectant and vapor barrier while allowing the optical signal to pass through to the detector (not shown).

Layer 49 acts as a vapor barrier from the outside—allowing sweat to evaporate through the device but no water from the exterior to enter. Polycarbonate membranes with pore sizes of 0.02–0.2 microns are satisfactory with 0.05 microns being preferred.

FIG. 4 is an overall view of the Drug Badge system of the present invention. As shown in FIG. 4a, the apparatus 50 is attached to the skin of a user by adhesive pads 52. Perspiration shown by arrows 54 containing drugs (diamond shapes) 56 moves in the direction of Arrow 57 which depicts the direction of fluid flow, as a result of the superabsorbent material contained in the badge, and the evaporation of the perspiration.

In FIG. 4b, the free drug 56 from the perspiration moves through the paper 58 where the covalently bound drug 59 is attached. The covalently bound drug 59 has antibodies 60 attached to it by standard antibody-antigen interaction. By virtue of competition for the antibody binding sites, the free drug from the perspiration 56 binds to the antibody to form a complex 62 of displaced labeled antibody and non-solid phase bound drug. This complex 62 then migrates to the bound anti-antibodies 64 which are then viewed by the photodetector 66. The filter and light sources are not shown in this drawing for simplicity.

FIG. 4c shows the entire assembled badge including the detection system 70 and the retention strap 72. An antenna for transmitting a signal can be built into the retention strap 72. The electronic transmission system is well known in the art and is presently in use in home detention systems and other similar devices, and therefore, is not separately described herein. FIG. 4d shows a reception unit 74 with an antenna 75 and a system for detecting receipt of a signal 76 indicating the presence of a chemical being detected and transmitting a signal to a remote receiver to forward that information.

It should be noted that the badge in FIG. 4c could be made up of cells, each one with a separate detector, or a detector that "poles" each cell. A multiple cell system is one way to detect more than one drug at a time (multiple labels is another).

When photodetector 66 detects the emission of light of a predetermined wavelength it sends a signal to a receiver which then, through any of a variety of means, such as telephone or electronic radio signal transmission, will signal a receiver that the drug, or other composition has been detected.

It will be appreciated by persons of skill in the art that other designs and processes to implement the present invention can be used without departing from the spirit and scope of the present invention.

EXAMPLE

The following is an example of use of the present invention in Pumped Flow-Through mode. See FIG. 5. This example uses Biotin as a drug analog.

Displacement Layer 90a

Cellulose, was chosen as the starting material for the displacement layer. Laboratory grade filter paper is a high purity material with uniform, well-characterized wetting properties that is robust and easy to handle. In addition the synthetic chemistry of its derivatization has been well established. Biotin derivatized filter paper was used in this example.

Trap Layer 92a

Beaded agarose was chosen as the packing material in the trap cell. Agarose is a common polysaccharide matrix used in low pressure liquid chromatography and there are a wealth of reagents available for covalently coupling ligands to it. Unlike most other matrix materials, agarose is relatively translucent. This helps the spectrofluorimeter "see through" the matrix and detect the bound fluorescence. Commercial preparations of Agarose for packing affinity columns consist of beaded 4% to 6% agarose. These products are available derivatized with a variety of active groups or ligands that are useful for BDC trap material: Protein-A, Protein-G, Anti-antibodies, Ion Exchange groups, etc. However, 4% agarose is not presently available in a form transparent enough for use in the trap cell. The lowest concentration of commercially available agarose beads is 1% and is sold underivatized for use in size exclusion chromatography. One percent agarose beads were obtained commercially and derivatized with ligand using techniques known in the art.

Normally, IgG (including goat IgG) is a cation (positively charged) at a pH near 7. However, IgG that has been highly derivatized with fluorescein isothiocyanate (FITC) may become anionic (negatively charged) at neutral pH. This is due to the decreased number of positively charged lysine residues and the added acidic character of the fluorescein molecule. This turned out to be the case with the FITC-label used in this example; therefore an anion exchange material was chosen for the trap material. N,N-diethyenediamine was coupled to 1% agarose beads with the CDI reaction (described in detail below): giving the agarose DEAE (diethylaminoethyl) anion exchange functionality.

Displacement Layer 90a Fabrication

The displacement layer is currently made from cellulose filter paper base. The filter paper (Whatman 3MM) is derivatized by conjugation with biotin via a synthetic reaction developed at the Naval Research Laboratory (NRL) by Dr. David Kidwell, the general approach of which is described here. A spacer arm is attached to the glucosidic hydroxyl groups of the cellulose fiber matrix of the paper. This, in turn, was further modified by conjugation with biotin. It will be recognized by persons of ordinary skill in the art that other chemistries well known in the art could be substituted here for the above biotin conjugation of the filter paper and would provide essentially the same result for the purposes of the present example of the present invention, namely biotin derivatized paper. After the derivatization steps the paper is cut into small disks (4 mm in diameter) and stored in a dry state. The disks were rehydrated with water and then washed with Mops Buffered Saline (MBS: 0.01M Mops (4-morpholinepropanesulfonic acid), 0.15M NaCl, pH 6.8) prior to reaction with dye conjugated antibiotin antibody.

Polyclonal antibodies were chosen for this test system. However, it is anticipated, that in its preferred form of the present invention the layer will be comprised of monoclonal antibodies of specific dissociation constants tailored to the operational life time and flow rates of the eventual field version of the device. To complete preparation of the displacement layer, fluorescein isothiocyanate labeled Goat anti-biotin (GAB-FITC) is incubated at 4° C. for a period of 24 hr at a concentration of 0.2 mg/ml with the biotin-paper in MOPS buffered saline (MBS) in the presence of 0.25% bovine serum albumin (BSA). The GAB-FITC attaches specifically to the solid phase biotin; the BSA minimizes nonspecific protein binding. The disk is then washed repeatedly with fresh MBS, and both disk and washes inspected for fluorescence with a UV lamp. The resultant displacement layer is stored in the dark at 4° C.

For flow testing, the disks were fitted into a Luer-lock adapter and placed into the flow path of a Perkin-Elmer HPLC apparatus. The apparatus consists of a buffer reservoir, pump, injector, and spectrofluorimeter (See FIG. 5). To minimize background signal the detector is located perpendicular to the excitation beam. The spectrofluorimeter operated at an excitation frequency of 490 nm and emission frequency of 520 nm.

Before actual testing with sample injections, the displacement disk was washed free of loosely-bound antibody by pumping buffer though the system until the fluorescence base line slope was essentially horizontal. Initial leaching of label was not surprising since the antibody employed is polyclonal and comprised of several distinct molecular species with differing affinities for the biotin on the conjugated paper. After sufficient washing, the labeled disks were ready to be tested for biotin detection sensitivity.

Trap 92a Fabrication

A "column" trap cell was fabricated for this pumped flow-through mode example. As previously discussed there are many matrixes available as the solid phase in the trap column. Agarose was chosen as the packing material in the current example trap cell. Because of their relative translucence, 1% agarose beads (100–200 mesh) were purchased from Bio-Rad Laboratories (Bio-Gel A150m) and derivatized in our laboratory. The derivatized agarose column trap layer acts like a 3 dimensional filter to trap fluorescent label detached from the displacement layer.

The agarose beads were derivatized according to the method of Bethell (G. S. Bethell; et al: Journal of Chromatography, 219 (1981) p361–371). Briefly, the agarose beads were activated with carbonyldiimidizole (CDI) in dioxane (anhydrous) solvent and then transferred to an aqueous carbonate buffer (1 molar pH 8.5–10) and incubated with the trap reagent. Imidazolyl carbamate was chosen because it reacts with available amino groups on the trapping reagents to form stable N-Alkyl carbamates under mild conditions as opposed to other possible matrix materials such as Epoxy activated materials, which require relatively harsh reaction conditions. Since the signal detected from the trap layer is based upon reporter dye molecule attached to the antibody, treatments limiting the non-specific binding of protein to the active matrix are not necessary. The trap reagents attach to the gel via their amino groups (lysine residues of proteins). The trapping reagent coupled to the agarose beads was 2-(diethylamino)-ethylamine. This provides the anion exchange functionality of diethylaminoethyl (DEAE).

For initial trap testing, the derivatized agarose beads were packed into a small glass flow column (0.2 ml packed volume in 1 cc syringe barrels) and equilibrated with 0.01M MOPS buffer pH 6.8 (MOPS). Following this step, 2 $\mu$g GAB-FITC in 400 $\mu$l MOPS was added to the column, and the column was washed with >1.5 ml MOPS. The column was then observed under UV illumination. Good tapping ability was indicated by a bright fluorescent band trapped near the top of the gel bed.

DEAE agarose was characterized for "quality of binding" of GAB FITC. The DEAE gel matrix was evaluated by increasing the salt content of the buffer, 0.01M MOPS pH 6.8, from zero to 2 molar NaCl. Results showed that there was no sharply defined salt concentration that would displace the FITC-GAB. Instead, the antibody was displaced starting at a NaCl concentration of 0.05M and was not completely removed until 2M. It was determined that zero salt gives the best binding with 0.05 molar a close second. However, 1.5M NaCl displaced most of the florescence from the column. The lack of a sharply-defined elution band indicates the GAB-FITC is heterogenous in ionic character. Sources of heterogeneity include: the antibodies' polyclonal nature, denaturation of the protein during purification/storage, and variable molar ratios of FITC to antibody which is reported to be an average F/P molar ratio of 3.7. While useful for determining optimum conditions for running the BDC flow tests, this ionic heterogeneity does not indicate any lack of performance of this reagent in the BDC.

The DEAE gel matrix column was adapted to the Spectrofluorimeter in its' own flow cell and flow tested with injections of GAB-FITC using MOPS buffer. With a relatively high flow rate of 0.5 ml/min and high hydrostatic pressure, the repeatability of the results were variable depending on the degree of compression of the gel. Changes in flow rates resulted in clearly visible changes in length of the trap layer material column. Since the gel is translucent and not transparent, compression causes a problem by changing the degree to which light scatters. This light cannot be completely distinguished from a true fluorescent signal due to the excellent but not perfect optical "filter" systems in the spectrofluorimeter. For the purposes of evaluating the material this problem was overcome by using an HPLC pump to precisely control the flow at a constant rate of 0.25 ml per minute. This caused minimal compression of the gel and therefore acceptable signal stability.

Compression artifacts are not anticipated to occur with the more ridged polymers available for use for the trapping matrix nor in the saturation/transpiration mode manifestations of the device because of the very low flow rates involved. For use as a "Drug Badge", the flow rate is on the order of 0.25 ml per day.

The testing of the trap layer material under these conditions demonstrated that it is capable of efficiently trapping the signal molecule. Aliquots of 0.1 μg of GAB-FITC delivered in a volume of 50 μl at a concentration of 2 μg/ml were injected into the flow stream and recovered with high efficiency as detectable fluorescence. Furthermore, multiple injections of five aliquots showed no evidence of trap layer saturation by the reporter molecule. Qualitative hand inspection of the column under ultraviolet light showed the visible band to be less than one millimeter in depth.

Pumped Flow-Through Mode BDC: flow testing.

The following text refers to FIG. 5.

A displacement layer cell 90 was mounted upstream of the trap column cell 92, and connected to it by flexible Tygon tubing 91, in a high pressure liquid chromatography (HPLC) system (however, run at low pressure). The displacement cell 90 consists of a displacement layer 90a of GAB-FITC antigenically bound to a biotin solid phase (described previously), and a glass wool layer 87a to support it. The trap cell 92 consists of a glass wool layer 87b supporting the trap matrix (previously described) of DEAE-agarose 92a.

Figure 6:
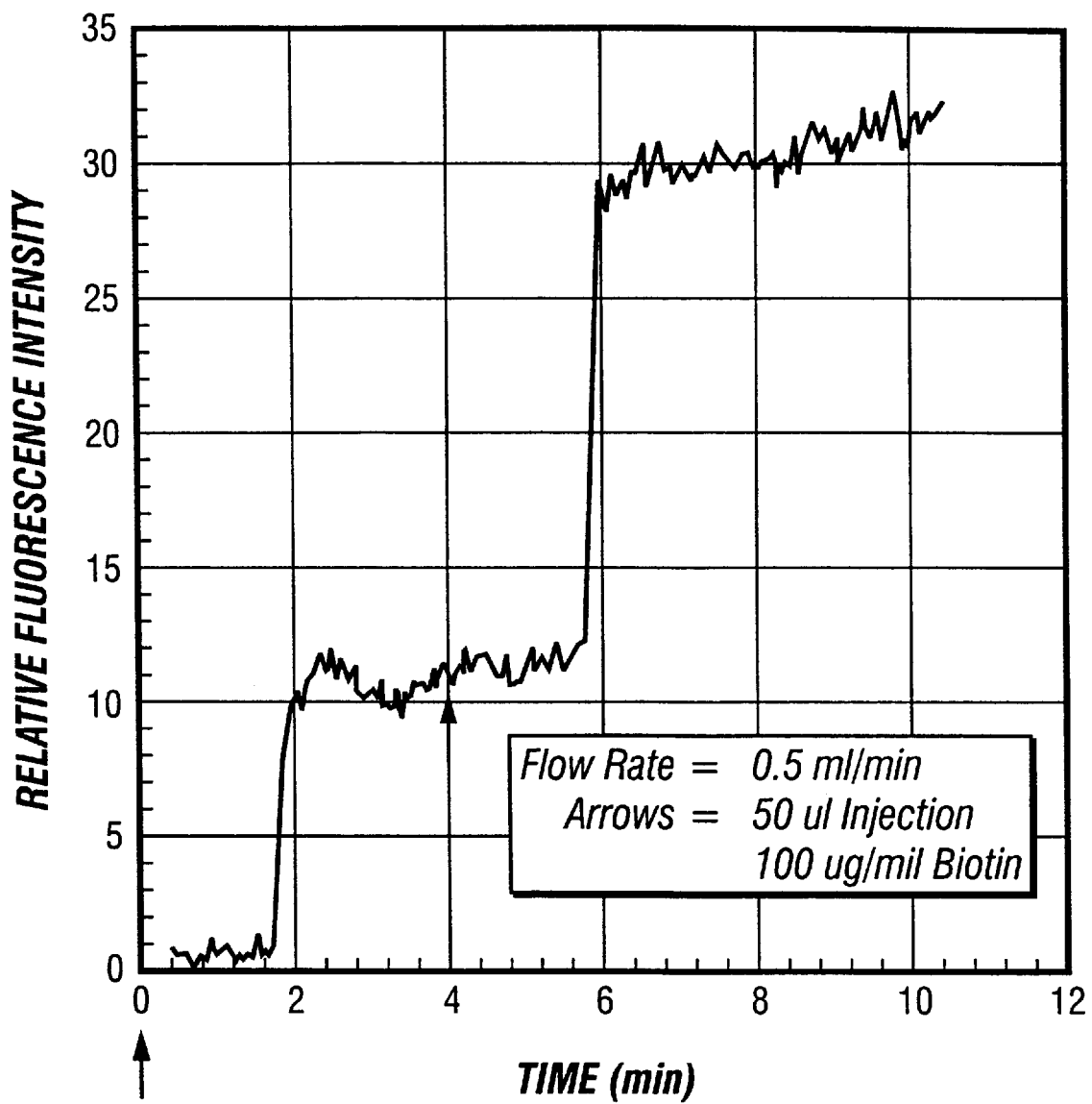
FIG. 6 shows results from the operation of the Pumped Flow-Through mode BDC of the example shown in FIG. 5.

The HPLC system is a Perkin-Elmer model 650-15 Fluorescence Spectrophotometer 94, with buffer reservoir 96, stainless steel tubing 91a, digitally controlled pump 93a, 50 μl sample injector 95, and recorder 97. The HPLC detector consists of a deuterium lamp light source 84a and a photomultiplier tube detector 84b. The BDC was operated in Mops Buffered Saline solution at a flow rate of 0.25 ml/min. 50 μl samples were injected into the flow stream. FIG. 6 shows results from injection of two 100 μg/ml samples over a 10 minute time period. As expected, the trap layer showed an increasing baseline with multiple injections of sample over time. The increasing baseline is indicative of the integration/amplification function of the trap layer. Data presented in FIG. 6 has been adjusted by a baseline subtraction algorithm to counter the effects of photobleaching of the fluorescein dye molecule. A more stable dye molecule such as Texas Red is to be preferred for the present invention. The device was able to detect the model compound across the middle of the concentration range found in clinical tests of perspiration for cocaine (0.034–317 μg/ml).

It will be appreciated by persons of skill in the art that other designs and processes to implement the present invention can be used without departing from the spirit and scope of the present invention.

What is claimed is:

1. An apparatus for detecting an analyte in the perspiration of a subject, said apparatus comprising:

a first layer, having a surface which facilitates attachment of the apparatus to the skin of the subject, having immobilized thereon the analyte to be detected;

said first layer further having labeled antibodies directed to said analyte, said labeled antibodies being of a type capable of linking to said immobilized analyte through an antigen-antibody linkage;

a second trap layer, adjacent the first layer, comprising an antibody immobilizing material therein, said antibody immobilizing material being directed against said labeled antibodies;

an optically and biochemically isolating spacer between said first layer and said second trap layer and formed of a material permitting said labeled antibodies to travel through it;

means for detecting the label on said labeled antibody, said detecting means positioned to detect when said labeled antibody is bound to said antibody immobilizing material of said second layer; and means, coupled to said means for detecting, for signaling a receiver when said means for detecting detects the labeled antibody bound to the antibody immobilizing material.

2. The apparatus of claim 1 further comprising a semipermeable membrane disposed below the first layer of said apparatus and adjacent the skin of the subject.

3. The apparatus of claim 1 wherein the analyte is covalently bound to said first layer.

4. The apparatus of claim 1 wherein said antibody immobilizing material is selected from the group consisting of anti-antibody, protein-A, protein-G, lectin, and ion exchange groups.

5. The apparatus of claim 1 wherein the labeled antibodies are labeled with a fluorescent, phosphorescent, enzyme, dyed-microsphere and other antibody label.

6. The apparatus of claim 1 wherein said means for detecting the label on said labeled antibody comprises a light emitting diode directed at said antibody immobilizing material for exciting the label on said labeled antibody, a filter or filters for reducing light emitted from said labeled antibody which is not within a predetermined wavelength range, and a photodetector for detecting the light emitted by the label.

7. The apparatus of claim 1 wherein the analyte to be detected comprises a drug of abuse.

8. The apparatus of claim 1 further comprising a means for holding said entire apparatus against the skin of the subject.

9. The apparatus of claim 1 wherein said optically isolating spacer is incorporated into the first layer.

10. The apparatus of claim 1 wherein said optically isolating spacer is incorporated into the second layer.

11. An apparatus for detecting an analyte in the perspiration of a subject, said apparatus comprising:

a first layer, having a surface which facilitates attachment of the apparatus to the skin of the subject, having immobilized thereon an anti-analyte antibody;

said first layer further having a labeled analyte to be detected bound by said immobilized anti-analyte antibody through an antigen-antibody linkage;

a second trap layer, adjacent the first layer, comprising an analyte immobilizing material therein, said analyte immobilizing material being directed against said labeled analyte;

an optically and biochemically isolating spacer between said first layer and said second trap layer and formed of a material permitting said labeled analyte to travel through it;

means for detecting the label on said labeled analyte, said detecting means positioned to detect when said labeled analyte is bound to said analyte immobilizing material of said second layer; and means, coupled to said means for detecting, for signaling a receiver when said means for detecting detects the labeled analyte bound to the analyte immobilizing material.

12. The apparatus of claim 11 further comprising a semipermeable membrane disposed below the first layer of said apparatus adjacent the skin of the subject.

13. The apparatus of claim 11 wherein the anti-analyte antibody is covalently bound to said first layer.

14. The apparatus of claim 11 wherein said labeled analyte immobilizing material is selected from the group consisting of anti-analyte antibodies, anti-label antibodies, protein-A, protein-G, lectin, and ion exchange groups.

15. The apparatus of claim 11 wherein the labeled analyte is labeled with a fluorescent, phosphorescent, enzyme, dye or dyed-microsphere label.

16. The apparatus of claim 11 wherein said means for detecting the label on said labeled analyte comprises a light emitting diode directed at said labeled analyte immobilizing material for exciting the label on said labeled analyte, a filter or filters for reducing light emitted from the label which is not within a predetermined wavelength range, and a photodetector for detecting the light emitted by the label.

17. The apparatus of claim 11 wherein the analyte to be detected comprises a drug of abuse.

18. The apparatus of claim 11 further comprising a means for holding said entire apparatus against the skin of the subject.

19. The apparatus of claim 11 wherein said optically isolating spacer is incorporated into the first layer.

20. The apparatus of claim 11 wherein said optically isolating spacer is incorporated into the second layer.

* * * * *